United States Patent
Hunt (10) Patent No.: US 11,484,070 B2
(45) Date of Patent: Nov. 1, 2022

(54) ONE-PIECE WASHABLE BRA LINER FOR NURSING MOTHERS

(71) Applicant: DAVIN & ADLEY LLC, Blackwood, NJ (US)

(72) Inventor: Amanda Hunt, Sewell, NJ (US)

(73) Assignee: DAVIN & ADLEY LLC, Blackwood, NJ (US)

( * ) Notice: Subject to any disclaimer, the term of this patent is extended or adjusted under 35 U.S.C. 154(b) by 189 days.

(21) Appl. No.: 17/069,278

(22) Filed: Oct. 13, 2020

(65) Prior Publication Data

US 2021/0112885 A1   Apr. 22, 2021

Related U.S. Application Data

(60) Provisional application No. 62/923,035, filed on Oct. 18, 2019.

(51) Int. Cl.
*A41C 3/04* (2006.01)

(52) U.S. Cl.
CPC .................... *A41C 3/04* (2013.01)

(58) Field of Classification Search
CPC .................. A41C 3/06; A41C 3/04
USPC .......................................... 450/37
See application file for complete search history.

(56) References Cited

U.S. PATENT DOCUMENTS

| | | | | |
|---|---|---|---|---|
| 2,627,606 | A * | 2/1953 | De Grandis | A41C 3/144 450/92 |
| 5,017,174 | A | 5/1991 | Gowrylow | |
| 7,776,019 | B2 | 8/2010 | Kawakami et al. | |
| 7,905,763 | B1 | 3/2011 | Frank | |
| 8,628,507 | B1 * | 1/2014 | Carroll | A61F 13/141 604/346 |
| 10,104,919 | B2 | 10/2018 | Perl | |
| 10,327,480 | B2 | 6/2019 | Khan | |
| 10,376,419 | B2 | 8/2019 | Lilien | |

(Continued)

FOREIGN PATENT DOCUMENTS

WO      2012087292 A1     6/2012

OTHER PUBLICATIONS

Nike Dri-FIT Swoosh Women's Medium-Support 1-Piece Pad Sports Bra, www.nike.com, 2020 [retrieved on Jun. 17, 2022] Retrieved from the Internet: <URL: https://www.nike.com/t/swoosh-womens-medium-support-1-piece-pad-sports-bra-sNSkxf/BV3636-100> (4 pages).

(Continued)

*Primary Examiner* — Timothy K Trieu
(74) *Attorney, Agent, or Firm* — Mendelsohn Dunleavy, P.C.; Steve Mendelsohn (57) ABSTRACT

A bra liner for nursing mothers to be placed inside the front cup area of a bra or top. In some embodiments, the pad is made from a bonded fabric, made up of 3 layers fused together with a melt-bond process. The bonded fabric combines absorbency, waterproofing, and leak protection into one material that is antimicrobial, hypoallergenic, and eco-friendly. The shape of an example bra liner is a horizontal figure eight with contoured cups and a narrow center connection. The cups have a single dart from the lower outside edge to the apex with zig-zag topstitching. The outside edge is clean finished with a thin, woven bias-cut binding set onto the fabric with a single row of stitching to prevent the fabric edges from unraveling while lying flat against the body.

11 Claims, 5 Drawing Sheets

(56) References Cited

U.S. PATENT DOCUMENTS

| | | | |
|---|---|---|---|
| 10,653,563 | B2 | 5/2020 | Lilien |
| 10,772,362 | B2 | 9/2020 | Corley |
| 2003/0220048 | A1 | 11/2003 | Toro et al. |
| 2012/0046627 | A1 | 2/2012 | Agnew |
| 2015/0335497 | A1 | 11/2015 | Montford |
| 2017/0252222 | A1* | 9/2017 | Marquez ............... A61F 13/141 |
| 2018/0077872 | A1* | 3/2018 | Maelfeyt ............... A01F 15/145 |
| 2018/0077972 | A1* | 3/2018 | Hinnershitz ............ A41C 3/04 |
| 2018/0317571 | A1* | 11/2018 | Caden .................... B32B 5/026 |
| 2020/0085113 | A1 | 3/2020 | Rendone |

OTHER PUBLICATIONS

TopBine Bra Pads Inserts, www.amazon.com, 2020 [retrieved on Jun. 17, 2022] Retrieved from the Internet: <URL: https://www.amazon.com/TopBine-One-pieces-Inserts-Removable-Swimsuit/dp/B094JFH7S2> (2 pages).

Women Swimsuit Padding Inserts Sponge Foam Bra Pads Chest Cup Insert Chest Pad, www.wish.com, 2020 [retrieved on Jun. 17, 2022 Retrieved from the Internet: <URL: https://www.wish.com/product/women-swimsuit-padding-inserts-sponge-foam-bra-pads-chest-cup-insert-chest-pad-5dce698a53a21f2f38b45036> (2 pages).

* cited by examiner

ONE-PIECE WASHABLE BRA LINER FOR NURSING MOTHERS

CROSS REFERENCE TO REPLACED APPLICATIONS

This application claims the benefit of U.S. Provisional Application No. 62/923,035, filed on Oct. 18, 2019, the entire disclosure of which is hereby incorporated by reference as if set forth fully herein.

BACKGROUND

Conventional nursing pads are used when a mother is lactating after childbirth to absorb leaking breastmilk into two separate circular-shaped absorbent pads. Either flat or contoured with an apex, each pad is placed over the center of one of the mother's breasts. There are many of these washable pads available to nursing mothers. They are made of multiple layers of absorbent and waterproof fabrics; however, the layers need to be stacked on top of each other and sewn around the edges to make one pad. The edges of these pads are very thick and bulky and show through the bra and clothing making large rings around the breasts. Mothers have to be concerned that the absorbent pads are visible and, when they show through clothing, it is often obvious and embarrassing.

SUMMARY

In certain embodiments, a bra liner includes a first contoured cup connected to a second contoured cup via a flexible narrow center connection, such that the bra liner forms the shape of a figure eight. The first and second contoured cups may be made of a fabric including at least one absorbent layer material comprising an antimicrobial finish, at least one liquid resistant layer material adjacent to the at least one absorbent layer material, and at least one smooth layer material adjacent to the at least one liquid resistant layer material. The bra liner also includes a binding edge bonding outer edges of the at least one absorbent layer material, the at least one liquid resistant layer material, and the at least one smooth layer material together.

In at least some of the foregoing embodiments, each of the first and second contoured cups includes one or more darts that extend from the outer edge to an apex of the contoured cup.

In at least some of the foregoing embodiments, the one or more darts may comprise a dart seam with a zig-zag stich on a top and a bottom of the one or more darts.

In at least some of the foregoing embodiments, each of the first and second contoured cups includes two or more darts that may extend from separate locations along the outer edge to an apex of the contoured cup.

In at least some of the foregoing embodiments, the bra liner may have a thickness of less than about 2 mm.

In at least some of the foregoing embodiments, the at least one liquid resistant layer material may include polyurethane.

In at least some of the foregoing embodiments, the at least one absorbent layer material may include polyester.

In at least some of the foregoing embodiments, the at least one absorbent layer may be an absorbent dimple layer.

In at least some of the foregoing embodiments, the at least one smooth layer material may have a polyester interlock fabric.

In at least some of the foregoing embodiments, the at least one absorbent layer material, the at least one liquid resistant layer material, and the at least one smooth layer material may be melt-bonded to form a bonded fabric.

In at least some of the foregoing embodiments, the anti-microbial finish may include silver ions.

In at least some of the foregoing embodiments, the bra liner may have a range of about 5% to about 20% stretch.

In at least some of the foregoing embodiments, the binding edge may be a woven bias binding.

In at least some of the foregoing embodiments, the binding edge may be about ¼ inch wide.

In at least some of the foregoing embodiments, distance from a top center edge portion of the first and second contoured cups to a corresponding bottom center edge portion of the first and second contoured cups may be greater than the distance from a top center edge portion of the flexible narrow center connection to a bottom center edge portion of the flexible narrow center connection.

In at least some of the foregoing embodiments, the distance from the top center edge portion of the flexible narrow center connection to a bottom center edge portion of the flexible narrow center connection is from about ¼ inch to about 2 inches.

In at least some of the foregoing embodiments, each of the first and second contoured cups is seamless and does not include a dart.

Additional details and advantages of the disclosure will be set forth in part in the description which follows, and/or may be learned by practice of the disclosure. The details and advantages of the disclosure may be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

Embodiments of the invention will become more fully apparent from the following detailed description, the appended claims, and the accompanying drawings in which like reference numerals identify similar or identical elements.

DETAILED DESCRIPTION OF THE INVENTION

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

The overall objective of this disclosure is to improve the design of nursing pads for lactating mothers.

One object of certain embodiments of the disclosure is to reduce the thickness of nursing pads (bra liners) and provide an improved design with a thinner fabrication but still offering the desired function of absorbing breastmilk and preventing it from leaking through to clothing.

Another object of certain embodiments of the disclosure is to provide a one-piece shaped nursing pad to stop individual circular pads from moving around inside the mother's bra or top during wearing.

An additional object of certain embodiments of the disclosure is to provide a nursing pad which gives modest coverage of the nipples when pregnant, breastfeeding, or pumping.

A further object of certain embodiments of the disclosure is to create a nursing pad with advanced moisture-absorbency technology that does not stay wet against the skin.

A further object of certain embodiments of the disclosure is to provide ease of washing nursing pads. The bra liner is able to be machine washable and dryable. With the one-piece shape, the pad cannot be separated from its pair or lost when washing.

A further object of certain embodiments of the disclosure is to add antimicrobial properties to the side of the pad that touches the skin and help reduce the risk for nipple infections.

Figure 1:
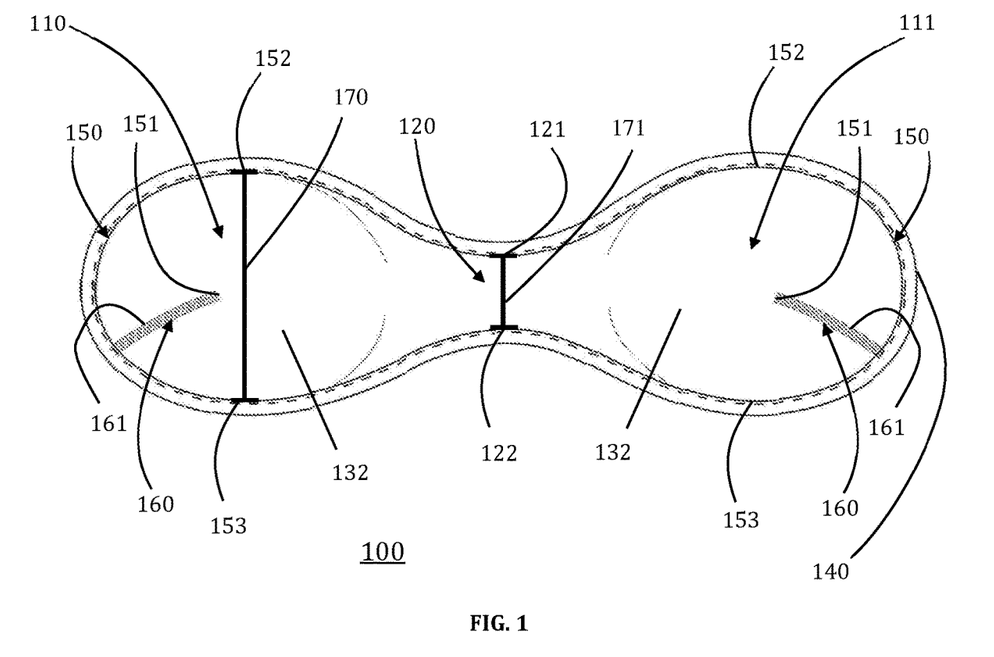
FIG. 1 is a top view of a bra liner according to one embodiment of the present disclosure.
Figure 2:
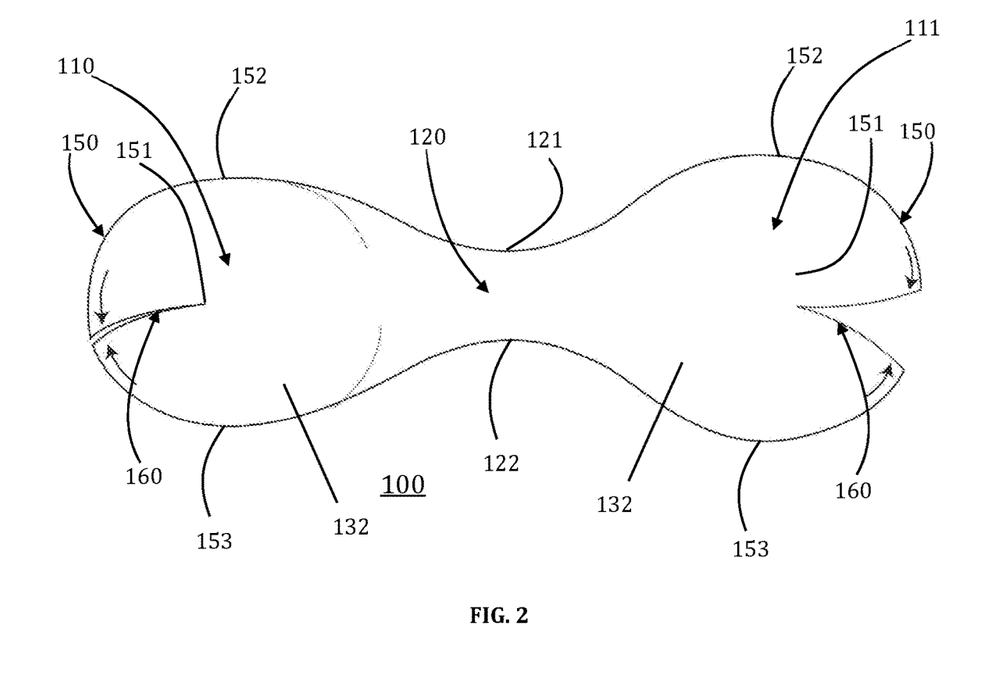
FIG. 2 is a top view of the bra liner of FIG. 1, without the binding edge.
Figure 3:
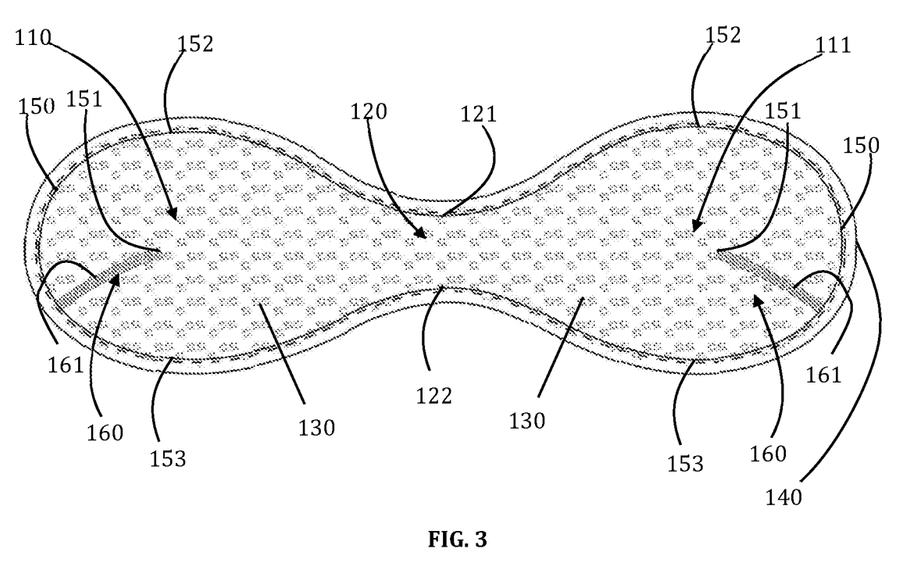
FIG. 3 is a bottom view of the bra liner in FIG. 1.
Figure 4:
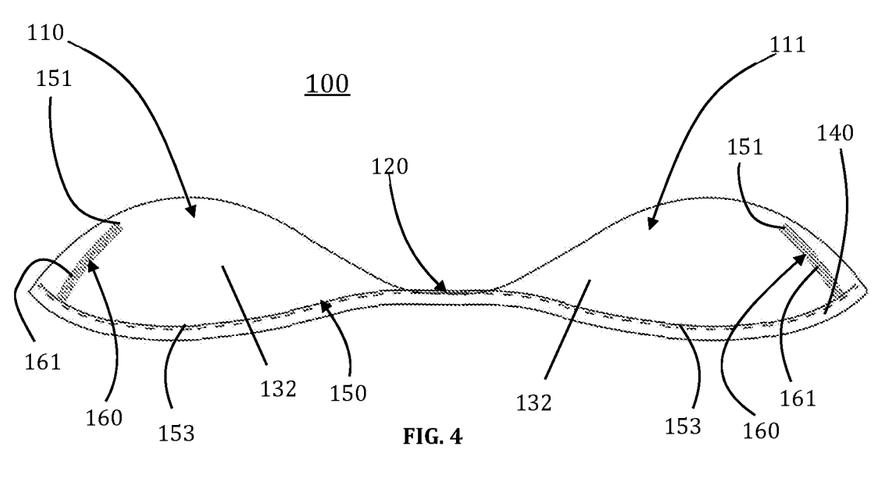
FIG. 4 is a horizontal side view of the bra liner of FIG. 1.
Figure 5:
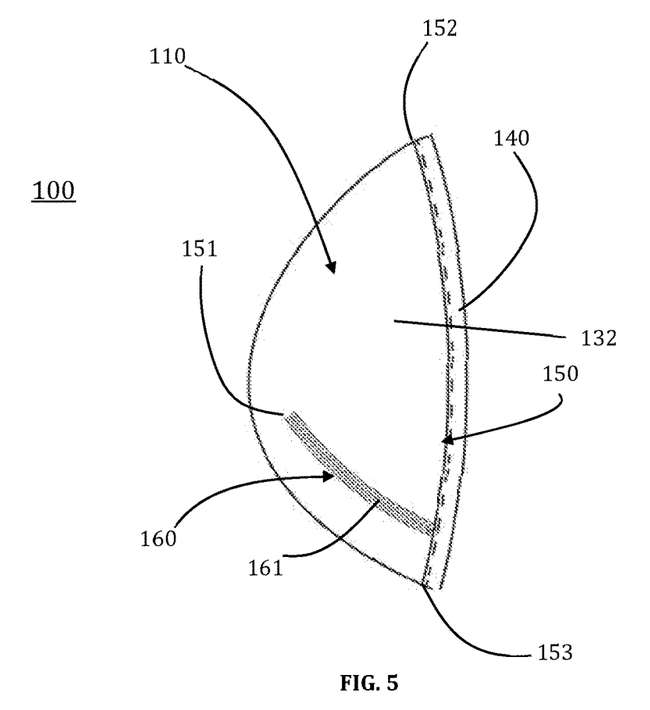
FIG. 5 is a vertical side view of the bra liner of FIG. 1.
Figure 6:
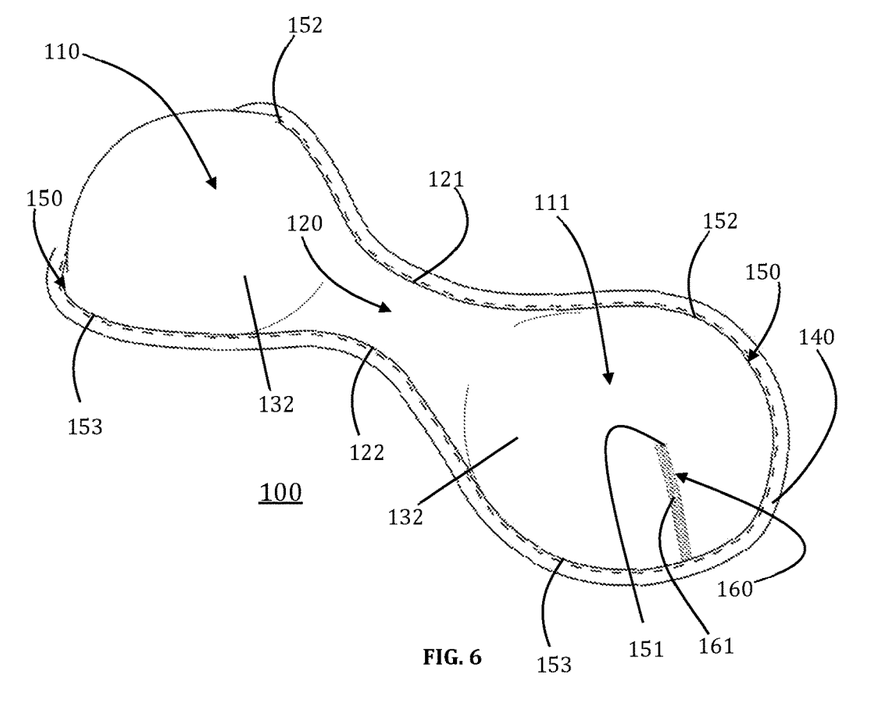
FIG. 6 is an isometric view of the bra liner of FIG. 1.
Figure 7:
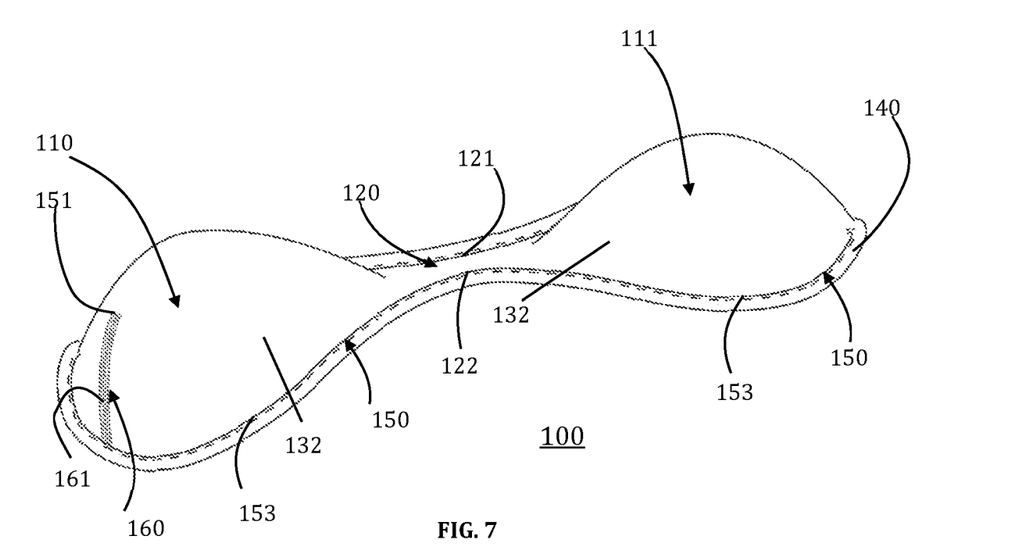
FIG. 7 is an alternative isometric view of the bra liner of FIG. 1.
Figure 8:
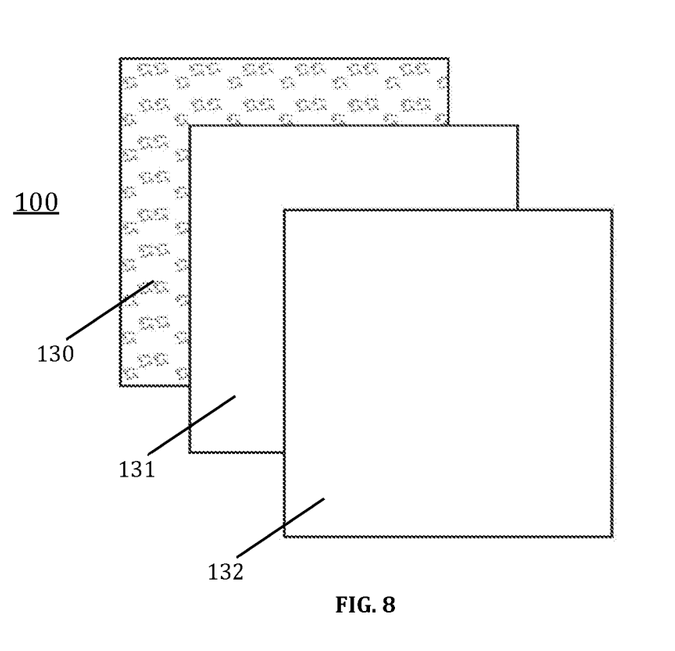
FIG. 8 is a view of the melt-bonded plurality of layers employed in the bra liner of FIG. 1.

FIG. 1 is a top view of a bra liner according to one embodiment of the present disclosure. FIG. 1 includes bars for indicating the distance of the contoured cups compared to the flexible narrow center connection 120. FIG. 2 is a top view of the bra liner of FIG. 1, without the binding edge. The left side of the drawing illustrates the dart being pulled together before sewing. The right side illustrates the fabric with the dart open. FIG. 3 is a bottom view of the bra liner in FIG. 1. This view illustrates the interior dimpled absorbent texture on the fabric. FIG. 4 is a horizontal side view of the bra liner of FIG. 1. FIG. 5 is a vertical side view of the bra liner of FIG. 1, showing the left side of bra liner in vertical position, the binding edge with woven bias binding with a single row of stitching, and a dart seam with zig-zag dart stitching. FIG. 6 is an isometric view of the bra liner of FIG. 1 showing the contoured shape of the cups. FIG. 7 is an alternative isometric view of the bra liner of FIG. 1 showing the contoured shape of the cups. FIG. 8 is a view of the melt-bonded plurality of layers employed in the bra liner of FIG. 1.

The unique shape of the bra liner of FIG. 1 is to improve the current function of nursing pads. When a mother has two separate circles placed on the breasts, they do not stay in the spots they are intended to. This makes it easy for the pads to slip down or come out of the bra and cause breastmilk to leak onto the clothing. The bra liner 100 of FIG. 1 includes a first contoured cup 110 connected to a second contoured cup 111 via a flexible narrow center connection 120 such that the bra liner 100 forms a horizontal figure-eight shape, which does not move once placed in the bra because the first contoured cup 110 and the second contoured cup 111 form a single piece with the flexible narrow center connection 120. The flexible narrow center connection 120 is narrow to provide flexibility between the breasts for a variety of breast shapes.

The bra liner 100 may accommodate bra sizes 32, 34, 36, 38, 40, 44, 46, 48, 50, 52, 54, and 56. The bra liner 100 may be increased in size by increasing the height and width of the first contoured cup 110 and second contoured cup 111 by 1-inch and 3-inch increments, respectively. The smallest bra liner 100 may be suitable for accommodating bra sizes 32, 34, and 36. The next incremental bra liner 100 may be suitable for accommodating bra sizes 38 and 40. The next incremental bra liner 100 may be suitable for accommodating bra sizes 42, 44, and 46, and so on. The depth of the first contoured cup 110 and second contoured cup 111 can adapt to all alpha bra sizes, and the amount of coverage will decrease as the breast size increases. Preferably, the bra liner 100 is suitable for cup sizes A-J. The bra liner 100 can also be made in larger sizes to accommodate larger breasts, such as band sizes 48-56 and cup sizes up to an M.

The flexible narrow center connection 120 which connects the first contoured cup 110 and the second contoured cup 111 forms the bra liner 100 into a figure-eight shape. The flexible narrow center connection 120 may be made from the same fabric as the first contoured cup 110 and the second contoured cup 111, to form a single continuous bra liner 100. Preferably, a first distance 170 from a top center edge portion of the first and second contoured cups 152 to a corresponding bottom center edge portion of the first and second contoured cups 153 is greater than a second distance 171 from a top center edge portion of the flexible narrow center connection 121 to a bottom center edge portion of the flexible narrow center connection 122. See FIG. 1. The flexible narrow center connection 120 may have a second distance 171 measured from a top center edge portion of the flexible narrow center connection 121 to a bottom center edge portion of the flexible narrow center connection 122 of from about ¼ inch to about 2 inches, or from about ½ inch to about 1 inch.

The fabric used for certain embodiments of this bra liner 100 is purchased at the mill as a bonded fabric made of a plurality of layers melt-bonded together. The fabric used for certain embodiments of this bra liner 100 is purchased at the mill as a bonded fabric made of a plurality of layers melt-bonded together. Preferably, the bonded fabric employed in the bra liner 100 may have a thickness of less than about 2 mm, or less than 1.75 mm, or about 1.65 mm while providing the same function as three thicker, unbonded fabric layers. This bonded fabric is more comfortable for the wearer and, with the layers bonded together, the bra liner 100 does not pucker or bunch inside the bra or top. Referring to FIG. 8, the melt-bonded fabric comprises of at least one absorbent layer material 130, at least one liquid resistant layer material 131, and at least one smooth layer material 132. The melt-bonded fabric may have about 5% stretch, or about 10% stretch, or about 15% stretch, or about 20% stretch, or from about 5% to about 20% stretch. In one embodiment, the first contoured cup 110 and the second contoured cup 111 are made from the melt-bonded fabric. In another embodiment, the first contoured cup 110, the second contoured cup 111, and the flexible narrow center connection 120 are made from the melt-bonded fabric. This embodiment is particularly advantageous in that the flexible narrow center connection 120 provides addition surface area to absorb addition fluids, e.g. breastmilk, sweat, etc.

The layer that is closest to the skin, i.e., the at least one absorbent layer material 130, may be 100% polyester. In some embodiments, the at least one absorbent layer material 130 is an absorbent dimple layer with absorbent dimples to absorb, disperse liquid, and lock in the moisture. See FIG. 3. The dimple layer is quick drying, so the fabric will not feel wet or cold when breastmilk has leaked.

Behind the at least one absorbent layer material 130 is the at least one liquid resistant layer material 131. The at least one liquid resistant layer material 131 may be an eco-friendly waterproofing 100% polyurethane film. This layer will not allow liquid to permeate through to the exterior.

The next layer is at least one smooth layer material 132. This layer may be a light 100% polyester interlock fabric. This layer is smooth and will not make bumps under clothing. Other suitable fabrications for this pad are bamboo and cotton, or mixtures thereof. The polyester interlock fabric and polyurethane film would also be melt-bonded to either the bamboo or cotton at the fabric mill.

The outer edge 150 of the bra liner 100 may be finished with a binding edge 140, selected from a woven bias binding, a knit bias binding, or other suitable methods for binding a seamless edge. The binding edge 140 may be sewn around the outer edge 150 of the bra liner 100 with, for example, a single row of stitching (FIG. 5) to prevent the plurality of layers from unraveling. The thin binding edge 140 provides an almost seamless shape and invisible appearance when worn under a bra and clothing. An alternative finish for the outer edge 140 may be an overlock stitch. This stitch is composed of threads looping over the edges of fabric. The bra liner 100 also provides a layer of coverage between the nipple and the bra. When a woman is pregnant, breastfeeding, or pumping, the nipples are elongated and may show under bras that do not have foam padding. This bra liner 100 gives mothers an option for a thin amount of coverage to be added to any existing bra or top. Preferably, the binding edge 140 has a width of about 1/16 inch to about 1/2 inch, or more preferably, from about 1/16 inch to about 1/4 inch.

An additional method of making this bra liner 100 is to laser cut the bonded fabric and apply a heat sealed or bonded edge along the bra liner. Bonding construction is a specific method of garment construction that does not involve a sewing machine and thread; only specialized adhesive tape and a heat press are used.

The first and second contoured cups 110 and 111 may each include one or more dart(s) 160 (FIG. 5) which may extend from the lower outer edge 140 to the apex 151 of each contoured cups 110, 111 and remains centered over the user's breast. The one or more dart(s) 160 include a corresponding dart seam 161 to close the dart, selected from a zig-zag stitch, a merrow stitch, a coverstitch, and other suitable alternative methods of sewing can be used. Another acceptable stitch is a merrow or coverstitch on the top and bottom of the one or more dart(s) 160. Another construction is to sew the one or more dart(s) 160 clean finished to the exterior with a merrow only on the interior and topstitch the merrow flat. An additional construction may employ bonding tape on the one or more dart(s) 160 for a flat and seamless appearance. In some embodiments, the bra liner 100 may include two or more darts 160, or three or more darts 160 along the outer edge 140 of each of the first and second contoured cups 110 and 111 to provide sufficient fullness.

This shape for the bra liner 100 is designed such that the bra liner 100 does not fall out of the mother's clothing with shifting or movement. This bra liner 100 shape is useful with athletic bras and tops having no defined cup shapes but can also be worn with bras that do have two separate cups. During breastfeeding, the mother can pull one breast out of the bra and the bra liner 100 will stay in place on the opposite side. Because the flexible narrow center connection 120 between the cups is narrow, each contoured cup 110, 111 can be moved as needed without removing the entire bra liner 100. When the mother is finished breastfeeding, the bra liner 100 is easy to put back into place because the opposite contoured cup 110, 111 remains centered over the other breast. With the conventional separate circular pads, each pad would be loose inside the bra, and as a result, the pad may be misplaced during breastfeeding.

The absorbent bra liner 100 soaks up excess breastmilk but because of the location of the bra liner 100 on the body, the fabric will additionally soak up sweat around the breast area. Both liquids have the potential to cause embarrassing odors. The fabric for this bra liner 100 may be treated with SILVADUR™ finish, an antimicrobial finish with silver ions, from Dupont Industrial Biosciences of Wilmington, Del. This finish is helpful to reduce the mother's risk for nipple infections and control feminine odor. Preferably, the antimicrobial finish is applied to the at least one absorbent layer material 130.

Conventional separate nursing pads are sold in pairs and very easy to misplace during the washing process. Some nursing pad manufacturers require hand wash and dry and others require machine washing and drying. There is additional drying time needed for items that cannot go in the dryer. The polyester fabrication for the bra liner 100 is recommended to be machine washed and dried. These are desirable care instructions to a busy mother that may not have time to wait for a pad to air dry. Because the bra liner 100 is one piece, there is no risk of misplacing one of the pads during washing. The improved shape is ideal for ease of washing.

Figure 9:
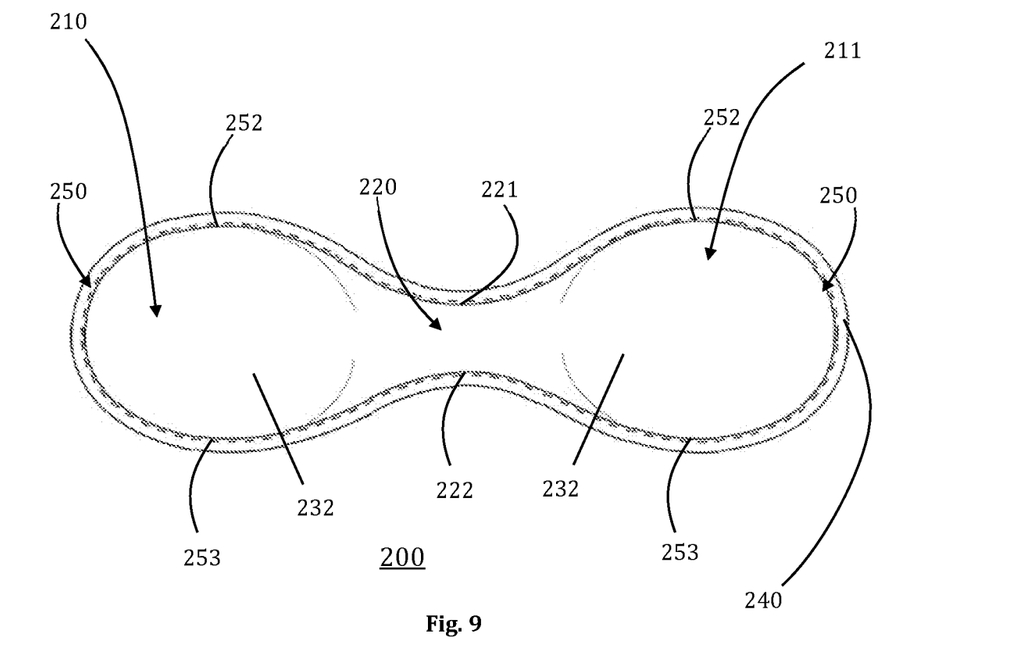
FIG. 9 is a top view of a bra liner according to another embodiment of the present disclosure.

FIG. 9 is a top view of a bra liner 200 according to another embodiment of the present disclosure. The bra liner 200 is similar to the bra liner 100 of FIGS. 1-8 with analogous elements having analogous labels. The first and second contoured cups 210 and 211 may be made with a heat set-mold. The desired cup shape would be created with a (e.g., metal) mold, and the heat would stretch the fabric to the contoured shape. This is also referred to as bulleting in bra making. In this embodiment, no darts are required to achieve the contoured cup shape, and the bra liner 200 would have a completely seamless appearance.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

What is claimed is:

1. A bra liner comprising:
a first contoured cup connected to a second contoured cup via a flexible narrow center connection, wherein the first and second contoured cups are made of a fabric comprising:
at least one absorbent layer material comprising an antimicrobial finish;
at least one liquid resistant layer material adjacent to the at least one absorbent layer material; and
at least one smooth layer material adjacent to the at least one liquid resistant layer material; and
a binding edge bonding outer edges of the at least one absorbent layer material, the at least one liquid resistant layer material, and the at least one smooth layer material together, wherein:
the at least one absorbent layer material, the at least one liquid resistant layer material, and the at least one smooth layer material are melt-bonded to form a bonded fabric having a total thickness of about 2 mm or less and a range of about 5% to about 20% stretch;
the flexible narrow center connection is made of the same fabric as the first and second contoured cups;
the at least one liquid resistant layer material comprises polyurethane;
the at least one absorbent layer material comprises an absorbent polyester layer;
the at least one smooth layer material is a polyester interlock fabric;
the binding edge is less than about' inch wide;
the distance from a top center edge portion of the first and second contoured cups to a corresponding bottom center edge portion of the first and second contoured cups is greater than the distance from a top center edge portion of the flexible narrow center connection to a bottom center edge portion of the flexible narrow center connection; and
the distance from a top center edge portion of the flexible narrow center connection to a bottom center edge portion of the flexible narrow center connection is from about ¼ inch to about 2 inches.

2. The bra liner of claim 1, wherein each of the first and second contoured cups comprises one or more darts that extend from the outer edge to an apex of the contoured cup.

3. The bra liner of claim 2, wherein the one or more darts comprise a dart seam with a zig-zag stitch on a top and a bottom of the one or more darts.

4. The bra liner of claim 1, wherein each of the first and second contoured cups comprises two or more darts that extend from separate locations along the outer edge to an apex of the contoured cup.

5. The bra liner of claim 1, wherein each of the first and second contoured cups is seamless.

6. The bra liner of claim 1, wherein the at least one absorbent layer is an absorbent dimple layer.

7. The bra liner of claim 1, wherein the anti-microbial finish comprises silver ions.

8. The bra liner of claim 1, wherein the binding edge is about ¼ inch wide and is a woven or knit bias binding.

9. The bra liner of claim 1, wherein:
the bonded fabric has a total thickness of about 1.65 mm;
wherein the at least one absorbent layer material comprises an absorbent polyester dimple layer;
wherein the anti-microbial finish comprises silver ions; and
wherein the binding edge is a woven bias binding and is about ¼ inch wide.

10. The bra liner of claim 9, wherein each of the first and second contoured cups comprises one or more darts that extend from the outer edge to an apex of the contoured cup.

11. The bra liner of claim 9, wherein each of the first and second contoured cups is seamless.

* * * * *

UNITED STATES PATENT AND TRADEMARK OFFICE
CERTIFICATE OF CORRECTION

| | |
|---|---|
| PATENT NO. | : 11,484,070 B2 |
| APPLICATION NO. | : 17/069278 |
| DATED | : November 1, 2022 |
| INVENTOR(S) | : Amanda Hunt |

It is certified that error appears in the above-identified patent and that said Letters Patent is hereby corrected as shown below:

In the Claims

In Column 8, Line 1, replace "the binding edge is less than about' inch wide;" with --the binding edge is less than about ½ inch wide;--.

Signed and Sealed this
Thirtieth Day of May, 2023

Katherine Kelly Vidal
*Director of the United States Patent and Trademark Office*